US 6,736,976 B2

(12) United States Patent
Kantzas et al.

(10) Patent No.: US 6,736,976 B2
(45) Date of Patent: May 18, 2004

(54) FLUID TREATMENT PROCESS

(76) Inventors: Apostolos Kantzas, 2500 University Avenue, Calgary, Alberta (CA), T2N 1N4; Cooper H. Langford, 2500 University Avenue, Calgary, Alberta (CA), T2N 1N4; Amit Bhargava, 2500 University Avenue, Calgary, Alberta (CA), T2N 1N4; Alex Starosud, 2500 University Avenue, Calgary, Alberta (CA), T2N 1N4

( * ) Notice: Subject to any disclaimer, the term of this patent is extended or adjusted under 35 U.S.C. 154(b) by 0 days.

(21) Appl. No.: 09/837,653

(22) Filed: Apr. 19, 2001

(65) Prior Publication Data

US 2002/0040874 A1 Apr. 11, 2002

Related U.S. Application Data

(60) Provisional application No. 60/198,448, filed on Apr. 19, 2000.

(51) Int. Cl.$^7$ .................................................. C02F 1/28
(52) U.S. Cl. .................. 210/661; 210/662; 210/668; 210/673; 210/677; 210/678; 210/679; 210/748
(58) Field of Search ........................ 210/661, 662, 210/668, 673, 677, 678, 679, 748, 96.1, 209, 266, 269

(56) References Cited

U.S. PATENT DOCUMENTS

| | | | | |
|---|---|---|---|---|
| 2,855,364 A | * | 10/1958 | Roberts .................... | 210/678 |
| 5,130,031 A | * | 7/1992 | Johnston ................... | 210/748 |
| 5,281,344 A | * | 1/1994 | Miller et al. ............... | 210/798 |
| 5,385,753 A | * | 1/1995 | Hu et al. ................... | 427/215 |
| 5,580,461 A | * | 12/1996 | Cairns et al. ............... | 210/673 |

* cited by examiner

Primary Examiner—Ivars C. Cintins
(74) Attorney, Agent, or Firm—Katten Muchin Zavis Rosenman

(57) ABSTRACT

A fluid treatment device for reducing the level of a chemical compound in a fluid. The device comprises: a fluid inlet; a fluid outlet; a flow-through fluid treatment zone having comprising: a radiation source, an adsorbent and a photocatalyst. The fluid treatment zone is reversibly operable between: (i) a first mode in which the fluid flows in a first direction and at least a portion of the chemical compound is adsorbed on the adsorbent; and (ii) a second mode in which the fluid flows in a second direction different from the first direction in which the absorbed chemical compound is exposed to radiation from the radiation resulting in photo-oxidation of the chemical compound.

14 Claims, 8 Drawing Sheets

—— Adsorption Cycle
- - - Regeneration Cycle

Effect of oxygen partial pressure on regeneration time

FLUID TREATMENT PROCESS

CROSS-REFERENCE TO RELATED APPLICATION

The present application claims the benefit, under 35 U.S.C. §119(e), of copending U.S. provisional patent application Ser. No. 60/198,448, filed on Apr. 19, 2000, the contents of which are hereby incorporated by reference.

BACKGROUND OF THE INVENTION

1. Field of the Invention

In one of its aspects, the present invention relates to a novel fluid treatment device. In another of its aspects, the present invention relates to a novel process for reducing the level of a chemical compound in a fluid.

2. Description of the Prior Art

Fluid treatment devices and processes are known.

Two approaches used in such devices and processes relates to adsorption and/or photocatalysis. Alone or in combination, these approaches are particularly suitable to remove or reduce the levels of a target contaminant in a fluid. In some cases, it is know to support a photocatalyst on an adsorbent. These approaches have met with some success to treat water containing one or more chemical compounds such as organic contaminants.

Much of the prior art has been devoted to improving the materials used to adsorb and/or photocatalyze the chemical compound(s) contained in the fluid. Generally, it has been seen to be desirable to increase one or more of the following properties of the material: adsorption capacity, adsorption rate and rate of photocatalysis.

Despite the advances made in the art, there is still room for improvement. For, example it would be desirable to have a practical and efficient device and process for treating fluid which did not necessarily require the use of high end adsorbents and photocatalysts. It would be further advantageous if the adsorption and photocatalysis could be conducted in the same fluid treatment zone.

SUMMARY OF THE INVENTION

It is an object of the present invention to provide a novel fluid treatment device which obviates or mitigates at least one of the above-mentioned disadvantages of the prior art.

It is another object of the present invention to provide a novel process for treatment of fluid which obviates or mitigates at least one of the above-mentioned disadvantages of the prior art.

Accordingly, in one of its aspects the present invention provides a fluid treatment device for reducing the level of a chemical compound in a fluid comprising:
  a fluid inlet;
  a fluid outlet;
  a flow-through fluid treatment zone-having comprising: a radiation source, an adsorbent and a photocatalyst;
  the fluid treatment zone reversibly operable between a first mode in which the fluid flows in a first direction and at least a portion of the chemical compound is adsorbed on the adsorbent; and a second mode in which the fluid flows in a second direction different from the first direction in which the adsorbed chemical compound is exposed to radiation from the radiation resulting in photooxidation of the chemical compound.

In another of its aspects, the present invention provides process for reducing the level of a chemical compound in a fluid, the process-comprising the steps of:
  feeding the fluid to a fluid treatment device comprising a fluid inlet; a fluid outlet and a flow-through fluid treatment zone disposed between the fluid inlet and the fluid outlet, the fluid treatment device comprising: a radiation source, an adsorbent and a photocatalyst,
  feeding the fluid in a first mode in which the fluid flows in a first direction and at least a portion of the chemical compound is adsorbed on the adsorbent; and
  feeding the fluid in a second mode in which the fluid flows in a second direction different from the first direction in which the adsorbed chemical compound is exposed to radiation from the radiation resulting in photooxidation of the chemical compound.

The present invention deviates from the conventional approaches to improve materials in that the present invention relies on practical and efficient cycling between adsorption mode and photocatalysis mode (this can also be consider to "de-adsorption" mode or "regeneration" mode). Thus, the present fluid treatment device is operable between a first adsorption mode and second photocatalysis (or regeneration or de-adsorption mode). In the adsorption mode, the chemical compound of interest is removed from the fluid being treated and is loaded onto the adsorbent—in this mode the adsorbent preferably is in the form of a fixed bed. When the loaded adsorbent reaches a predetermined threshold, fluid flow through treatment zone is, in a preferred embodiment, reversed and radiation from the radiation source serves to photocatalyze the loaded adsorbent—in this mode the photocatalyst preferably is in the form of a fluidized bed. Preferably, the adsorbent and the photocatalyst are comprised in the same material (e.g., the photocatalyst is supported on the adsorbent).

BRIEF DESCRIPTION OF THE DRAWINGS

Embodiments of the present invention will be described with reference to the accompanying drawings, wherein like numerals designate like elements, and in which.

DETAILED DESCRIPTION OF THE PREFERRED EMBODIMENTS

Figure 1:
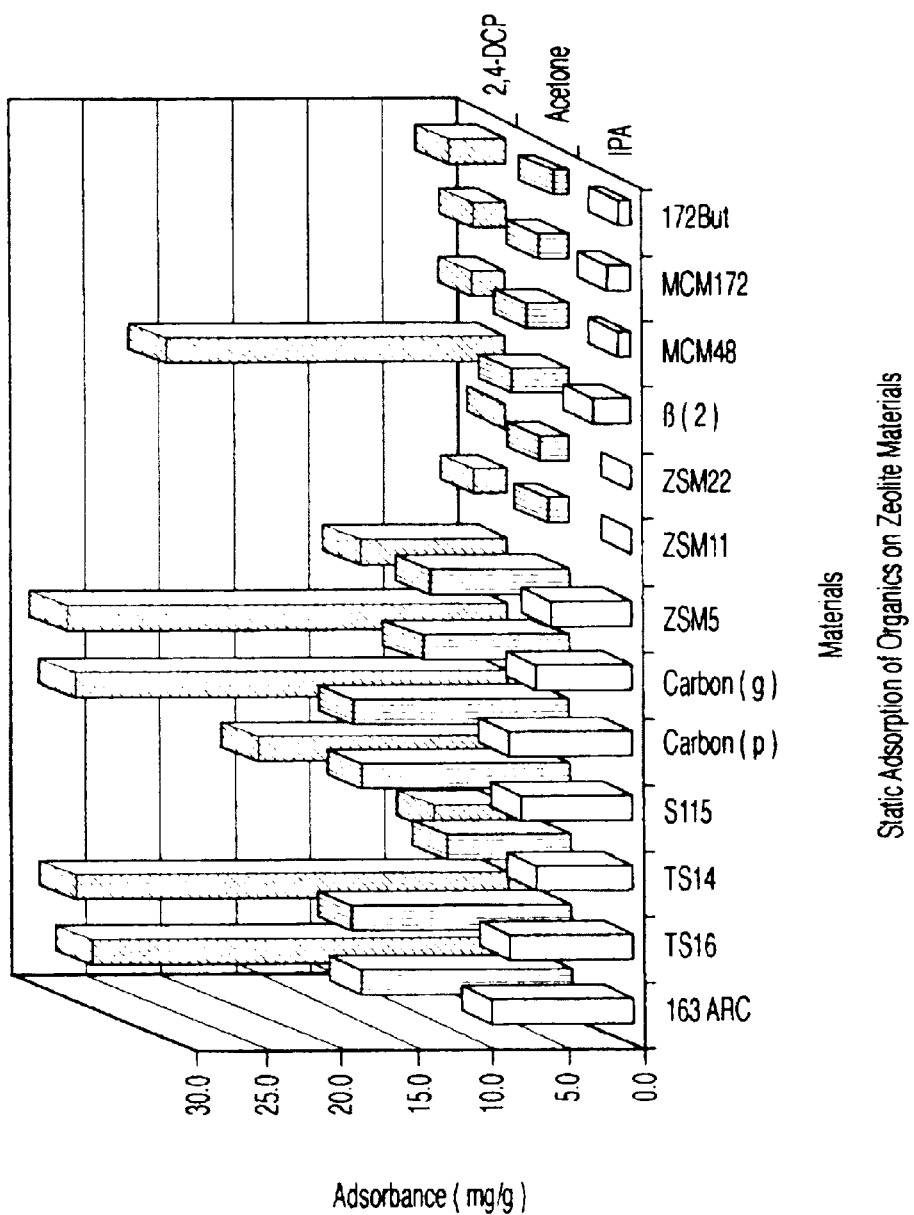
FIG. 1 illustrates static adsorption of organic materials on zeolite materials.

Thus, in one of its aspects, the fluid treatment device for reducing the level of a chemical compound in a fluid comprising:
  a fluid inlet;
  a fluid outlet;
  a flow-through fluid treatment zone having comprising: a radiation source, an adsorbent and a photocatalyst;
  the fluid treatment zone reversibly operable between a first mode in which the fluid flows in a first direction and at least a portion of the chemical compound is adsorbed on the adsorbent; and a second mode in which the fluid flows in a second direction different from the first direction in which the adsorbed chemical compound is exposed to radiation from the radiation resulting in photooxidation of the chemical compound.

Preferably, in the first mode, the adsorbent comprises a fixed bed.

Preferably, in the second mode, the photocatalyst comprises a fluidized bed.

The nature of the photocatalyst is not particularly restricted. Preferably, the photocatalyst comprises $TiO_2$.

The nature of the adsorbant is not particularly restricted. Preferably, the adsorbent comprises a member selected from the group comprising a zeolite, a ceramic and mixtures thereof.

Preferably at least one, more preferably both, of the adsorbent and the photocatalyst is particulate.

In a particularly preferred embodiment, the adsorbent and the photocatalyst are comprised in the same material (e.g., particulate material), for example by loading or otherwise supporting, bonding or adhering the photocatalyst on to the adsorbent.

Preferably, the radiation source comprises an ultraviolet radiation source.

Alternatively, the radiation source comprises a visible radiation source.

The fluid to be treated by the present device comprises a liquid, preferably air. Alternatively, the fluid to be treated by the present device comprises a gas.

In one preferred embodiment, the fluid flows through the treatment zone in the first direction and in the second mode, the fluid flows through the treatment zone in the second direction. More preferably, wherein the first direction and the second direction are substantially opposed to one another.

While the physical nature of the radiation source is not particularly restricted, preferably it elongate and comprises a longitudinal axis. Preferably, the longitudinal axis is aligned substantially parallel to one, more preferably both, of the first direction and the second direction.

Preferably, the radiation source is at least partially, preferably substantially completely, immersed in fluid flowing through the treatment zone. Practically, it may be beneficial to dispose the radiation source in a protective sleeve substantially transparent to radiation emitted from the radiation source. Preferably, the protective sleeve comprises a quartz sleeve.

Alternatively, the radiation source may be disposed exteriorly of fluid flowing through the treatment zone. This may be achieved, for example, by disposing the radiation source adjacent to a treatment zone housing made of a radiation transparent material.

Preferably, the radiation source is operable in the second mode or in both the first mode and the second mode.

In a further preferred embodiment, the fluid treatment zone comprises a screen or other suitable sieve-like means adapted to allow concurrent fluid flow through the fluid treatment zone and retention of the adsorbent material and the photocatalyst in the fluid treatment zone. In other word, the screen, together with the walls of the fluid treatment zone functions as a basket to retain the adsorbent material and photocatalyst in place while fluid is passed through the fluid treatment zone.

The nature of the chemical compound to be treated in the present device and process is not particularly restricted. Thus, the chemical compound may be organic or inorganic.

In a particularly preferred embodiment of the present fluid treatment device, there is provided a first controller for switching from the first mode (e.g., adsorption) to the second mode (e.g., regeneration) when a predetermined amount of the chemical compound has been adsorbed on the adsorbent. It is also preferred to include a second controller for switching from the second mode (e.g., regeneration) to the first mode (e.g., adsorption) when a predetermined amount of the chemical compound has been photocatalyzed.

Practically and, in some cases preferably, a plurality of the present fluid treatment devices are employed in a larger fluid treatment system. In this situation, it is preferred that the fluid treatment system additionally comprise a controller for operation of a first subset of the plurality of fluid treatment devices in the first mode (e.g., adsorption) and a second subset of the plurality of fluid treatment devices in the second mode (e.g., regeneration).

During the present process, it is preferred to switch, from the first mode to the second mode when a predetermined amount of the chemical compound has been adsorbed on the adsorbent. Further, it is preferred to switch from the second mode to the first mode when a predetermined amount of the chemical compound has been photocatalyzed.

Non-limiting embodiments of the present invention will be described with reference to the following Examples which should not be used to construe or limit the scope of the invention.

EXAMPLES

Heterogeneous photocatalysis offers an attractive alternative for wastewater treatment especially when treating low concentrated, high volume fluids. For the photocatalytic process, a preferred photocatalyst material is titania or titanium dioxide ($TiO_2$). It is characterized, relatively, by chemical inertness, non-photocorrosivity and nontoxic influence on microorganisms. These properties of titanium dioxide, coupled with its ability to create highly reactive oxidant (hydroxyl radical) on excitation with UV radiation, make titanium compounds highly suitable for application in wastewater treatment. The hydroxyl radical (OH.) which is known to be one of the most powerful oxidizing species, mineralizes organic pollutants to carbon dioxide and inorganic ions.

The efficiency of photocatalytic reactors using immobilized photocatalysts have been found to be lower than those using dispersed titania particles (slurry).

Application of fine powder of $TiO_2$ is technologically impracticable because powders could be easily washed out. To deal with this phenomenon, a need for additional equipment to be constructed may arise [1] which, unfortunately, causes a sharp rise in the cost of the process.

There is a practical preference to immobilize titania [1,2]. Many attempts have been made using glass beads, fiber glass, silicon, quartz, activated carbon and zeolites as support [1,2,3].

Zeolites, as a photocatalyst support, offer the advantage of having relatively high adsorption for organics in wastewater thereby facilitating preconcentrating of pollutants on their surface.

We have synthesized and tested as supports more than 40 different types of zeolites and their modifications. All of the synthesized materials can be divided in four classes:
  (i) mesoporous molecular sieves (MCM-41) and relatives thereof;
  (ii) titanium silicates (TS class with Ti incorporated into zeolite lattice) of both micro- and meso-pore types;

(iii) aluminophosphates sieves (VPI-5) and relatives containing both Si and Si—Ti ; and (iv) siliceous zeolites of the MFI and MEL structure families (TS-16, ZSM 48, etc.).

Adsorption characteristics of all synthesized materials were evaluated using static conditions. The static experiments involved slurring the material into solutions of organic contaminants for periods up to 48 hours. The aliquot and filtrate were analyzed by HPLC or GC.

Most of these synthesized zeolites exhibited relatively low adsorption toward chosen contaminants as compared to activated carbon as a standard. Some results for isopronanol (IPA), acetone and 2,4-dichlorphenol (DCP) are illustrated in FIG. 1 for the more preferred materials.

The major rival for zeolite materials is activated carbon. From FIG. 1, it can be seen clearly that two of the materials (163ARC and TS-16) have nearly the same capacity as carbon and are even superior toward polar contaminants (acetone, IPA).

The preferred zeolites were loaded with titania to obtain an integrated photocatalyst-adsorbent system (IPCA).

$TiO_2$, loading was accomplished by stirring the zeolite with a previously prepared colloid of $TiO_2$, evaporating the solvent, and calcining the resultant solid at a temperature between 200° C. and 500° C. This was the preferred method of $TiO_2$ loading which has been identified in earlier work [4]. Two modifications were also used. First, the standard colloid with particle size in 10 nm and higher range were replaced with a preparation of "quantum size" or "Q-sized" particles of 2–4 nm size [5]. A further modification with loading Q-sized particles under these conditions, in this case filtration, replaced evaporation of solvent.

Physical characterization of IPCA included Raman spectroscopy to examine the state of $TiO_2$, scanning, electron microscopy (SEM) and Si—H CP-MAS NMR spectroscopy to identify $TiO_2$ clustering and X-ray diffraction (XRD) to verify the identity of the zeolite phases and the apparent particle size in $TiO_2$ loading. An interesting result is that all $TiO_2$ reflections in XRD have line width suggesting particle size smaller than the size of colloidal $TiO_2$ particles used in loading onto the support.

In light of these findings, $TiO_2$ distribution was investigated.

A novel energy filtered transmission electron microscopy technique was used to obtain a Ti distribution map [6]. It was found that whenever zeolite pores are smaller than the particle size of $TiO_2$, the colloidal particles used in loading titania remains on the surface.

For general screening of photocatalytic behavior of IPCA, a larger diameter Teflon cell with a quartz window at the top was used. Several of these could be irradiated simultaneously under a pair of 40W fluorescent ultraviolet (UV) lamps with peak output at 350 nm. Substrate oxidation was measured using a mass balance approach where reduction of solution concentration was monitored and IPCA's were extracted with organic solvent at the end of runs to recover any material adsorbed.

The overall results of screening for photocatalytic activity can be summarized as follows:

(i) a conventional MCM-41 exhibited higher activities than zeolite Y (used as a reference);

(ii) titanium silicates showed very low activity;

(iii) silicon- and titanium-containing aluminophosphates had low activity;

(iv) several members of MFI and MEL families were quite active.

Unfortunately, the adsorption characteristics of MCM-41 class are not optimal, so efforts were focussed on the MFI and MEL family of materials. Several synthesized systems, including ZSM-48, ZSM-11 and TS-16 are particularly preferred. As well, commercial ZSM-5 and silicalite I are preferred.

In order to reduce the cost of the IPCA, a prospective new approach may be as follows. The general idea was to use inexpensive, and readily available particles with a desired diameter as a carrier for titania and zeolite. The carrier should be mechanically strong, should not reduce photoactivity and have a "golfball" like surface to reduce attrition of zeolite/titania by depressions.

For heterogeneous photocatalytic reactions, it is preferred to maximize the contact among reactants, photons and photocatalysts. Mixing and flow characteristics of the photoreactor may greatly enhance these contacts. If a conventional fixed bed reactor is used, the irradiated aliquot of photocatalyst is limited to a thin layer and a large reactor volume is required. For conventional liquid-solid and gas-solid systems, continuously stirred tank photoreactors and fluidized bed photoreactors, respectively, are conventional systems for enhancing contact efficiency—however, operation of these systems is quite expensive and troublesome. The rate of photocatalytic reaction is greatly affected by flow rates. The rate enhancement is not due to elimination of mass transport resistances, as expected in classical catalytic systems, since such considerations do not substantially apply for most heterogeneous photo-processes that are characterized by low reaction rate with respect to mass transport rate. The enhancement is determined by the fact that on increasing flow rates, the frequency of exposure of the photocatalyst particles to irradiation increases. The photocatalyst particles continuously receive diffuse radiation of reduced intensity due to absorption by other photocatalyst particles. They are directly irradiated intermittently due to shielding effect of particles which randomly intercept direct irradiation. By increasing flow rates, the frequency with which the photocatalyst particles may be directly irradiated increases and eventually, the reaction rate is enhanced.

Figure 2:
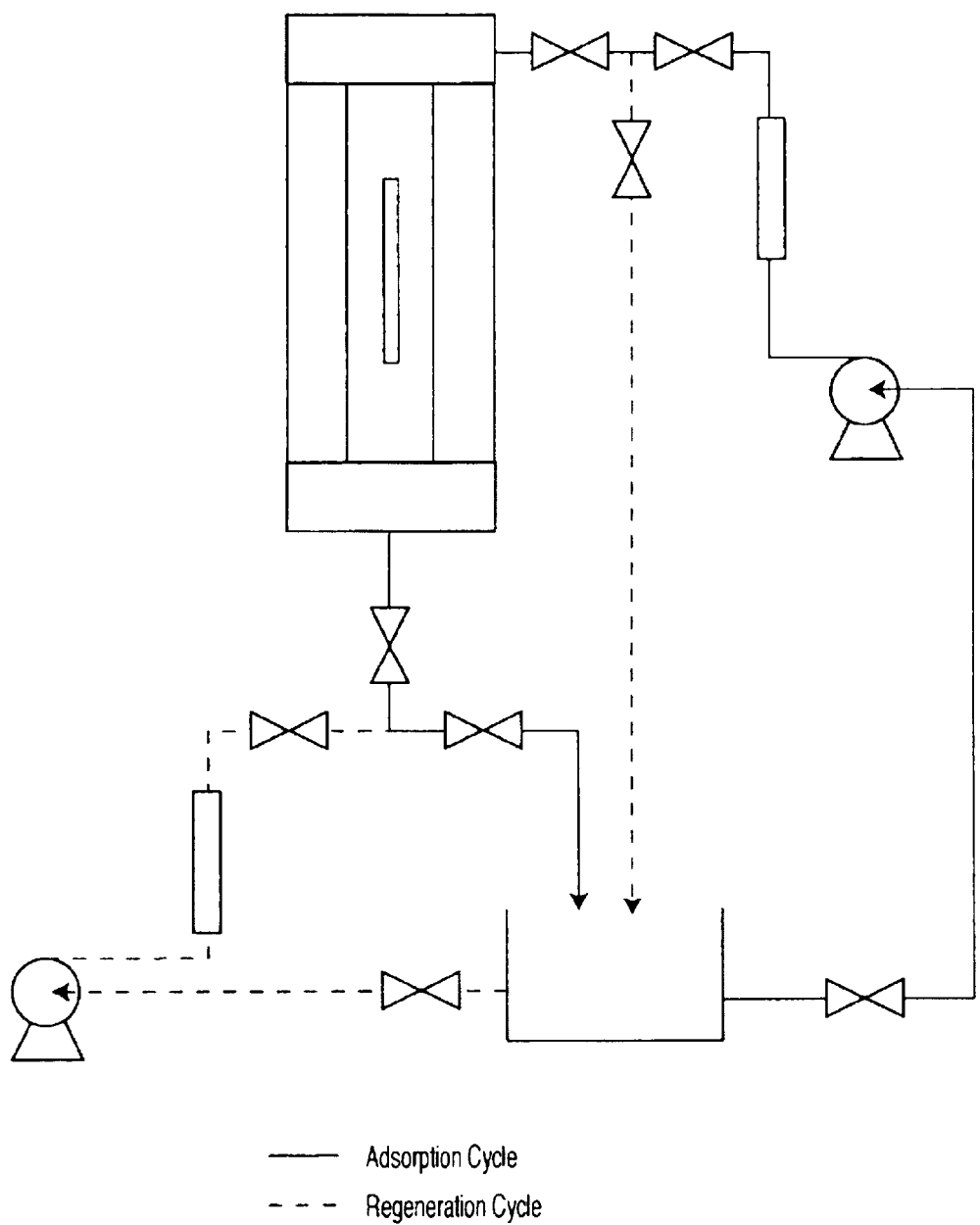
FIG. 2 illustrates a schematic of a preferred embodiment of the present fluid treatment device.

In light of these problems with conventional approaches, an annular liquid fluidized bed photocatalytic batch reactor with full recirculation was constructed. A schematic of the reactor showing the adsorption and regeneration cycles is depicted in FIG. 2. The reactor was then modelled (i.e., the operation thereof was modelled) based on the study done by Rideh et. al. [7]. In this kind of reactor, the extended light source is placed at the axis of a reactor composed of two coaxial cylindrical tubes. The emitted radiant power is absorbed by the reaction system contained in the annular reactor volume. Irradiance diminishes in a filled reactor with increasing radius. This geometry, called the "negative geometry" of irradiation makes the most efficient use of the light emitted by an extended light source. In fact, this geometry is used in all immersion type photochemical reactors, and most industrial photochemical production units [10].

In these Examples, a liquid fluidized bed photocatalytic reactor for 2-chlorophenol degradation operating in once through and dual mode (adsorption followed by regeneration) was modelled and simulated. Also, to analyze the effect of various operational parameters such as initial pollutant concentration, flow rate, oxygen partial pressure, absorbed LV light intensity and initial bed height were varied using the developed simulator with a view to assessing the range of operational parameters for preferred reactor performance.

A hydrodynamic model was set up using the Wen and Yu Correlation [8] to predict the bed voidage as a function of superficial velocity. The number of particles in the elemental volume under consideration were calculated using geometry. The average light intensity reaching a photocatalyst particle surface was arrived at using the line source with parallel plane (LSPP) emission model [9]. In this model, the lamp is considered to be a linear source in which each point emits radiation in parallel planes perpendicular to the lamp axis. Combining this hypothesis with the Beer-Lambert equation, the integration of the differential equation describing the radiant power or irradiance as a function of the optical path yields the profile of radiant power or irradiance.

Kinetic modeling of the primary degradation steps is important for practical application of the process. Rideh et al. [7] showed that 2-chlorophenol was degraded in an illuminated suspension of $TiO_2$ according to the following stoichiometry:

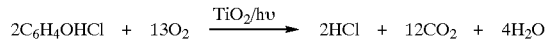

A pseudo-plug flow model has been used to simulate the process. A number of discrete plug flow reactors of an annular shape have been considered to represent the reactor. The assumptions used in the development of model are:

(i) Complete radial mixing and no axial mixing in the elemental volume;

(ii) No mixing between the adjacent annular PFR's;

(iii) no reaction in the part of the reactor above the expanded bed (i.e., no direct photolysis);

(iv) even distribution of photocatalyst particles in the expanded bed region;

(v) same inlet concentration to all the annular PFR's; and (vi) complete mixing of the wastewater while effluent is recirculated.

Total number of particles in the reactor can be calculated from the voidage and height of bed at minimum fluidization:

$$N_P = \frac{3}{4} \frac{(1-\varepsilon_{mf})(R_O^2 - R_I^2)H_{mf}}{r_P^3}$$

Particle number density in the expanded bed region can be calculated from the total number of particles in the reactor, assuming equal distribution of particles in the expanded bed region:

$$N_{PD} = \frac{N_P}{\pi(R_O^2 - R_I^2)H_{EX}}$$

where, the expanded bed height is calculated from the voidage predicted by Wen & Yu Correlation:

$$H_{EX} = \frac{(1-\varepsilon_{mf})}{(1-\varepsilon)} H_{mf}$$

Thus, number of particles in the elemental volume can be calculated as:

$$n_P = N_{PD}\pi(R_O^2 - R_I^2)\Delta Z$$

The light intensity incident to elemental volume under consideration is given by the LSPP Emission Model:

$$I_{Inc} = \frac{S_{L,\lambda}\exp[-\mu(r-R_I)]}{\pi(R_o^2 - R_I^2)}$$

Hence, the net light intensity absorbed by the photocatalyst particles present in the elemental volume is given by:

$$I_{Abs} = \frac{I_{Inc}n_P\pi r_P^2}{2\pi r \Delta z}\alpha\beta$$

wherein:
  $\alpha$=fraction of particles which are irradiated by the incident photons; and
  $\beta$=fraction of incident light intensity absorbed Material balance based on the amount of poflutant (2-chlorophenol) inside the elemental volume can be written at steady state as follows:

[Mass of 2-CP in]−[Mass of 2-CP out]−[Mass of 2-CT degraded by photocatalysis]=[Accumulation]

At steady-state, [Accumulation]=0.
Also:

[Mass transfer of 2-CP from bulk to photocatalyst surface]=[Mass of 2-CP degraded by photocatalysis]

$Q.(C_i)_{r,z} - Q.(C_i)_{r,z+\Delta z} = A.\Delta z.(\text{rate})$ $$\frac{dC_i}{dz} = -\frac{(\text{rate})}{U_L}$$

$$\int \frac{dC_i}{(\text{rate})} = -\frac{1}{U_L}\int dz$$

where, the rate expression is evaluated in the same manner as taught by Rideh et al. [7].

A similar material balance conducted for 2-CP in the bulk liquid and solid photocatalyst phase results in a set of differential equations as follows.

For bulk liquid phase:

$$\frac{dC_L}{dz} = \frac{1}{u}\int k_L a(C_S - C_L)$$

For solid photocatalyst phase:

$$\frac{dC_S}{dz} = -\int \frac{A}{W}\left[k_L a(C_S - C_L) + k_r'k'I_{abs}^n C_{O_2}^n C_S\right]$$

The liquid-solid mass transfer coefficient was evaluated using the correlation proposed by Hassanien et al. [11]:

$$Sh = 0.33(Ga.Mv.Sc)^{1/3}[1+0.22Mv^{-0.57}(U_G/U_L)^{0.77}]$$

The material balance conducted for the pollutant in the liquid and solid phase in a PFR over the elemental volume at a fixed radial distance resulted in a set of simultaneous first-order ordinary differential equations. The equations were solved numerically using fourth order Runge-Kutta method with adaptive step-size control to obtain 2-CP concentrations at various axial distances. The above steps were carried out for all the annular PFRs.

The values of 2-CP concentrations obtained at the outlet of the reactor were then averaged and formed a new initial concentration to the inlet of the reactor for the next time step. The same procedure was repeated for a number of circulations to obtain 2-CP concentrations at the outlet of the reactor corresponding to time.

For the adsorption cycle, break-through of the photocatalyst bed was considered when more than 95% of it was saturated. For the regeneration cycle, the photocatalyst bed was considered to be regenerated when 99% of the initial adsorbed concentration was removed from the solid phase due to reaction or transfer to the bulk liquid phase.

The dimensions and process variables required as an input for the simulations are presented in Table 1.

The model for the once through process was run using the above process variables and dimensions.

Figure 3:
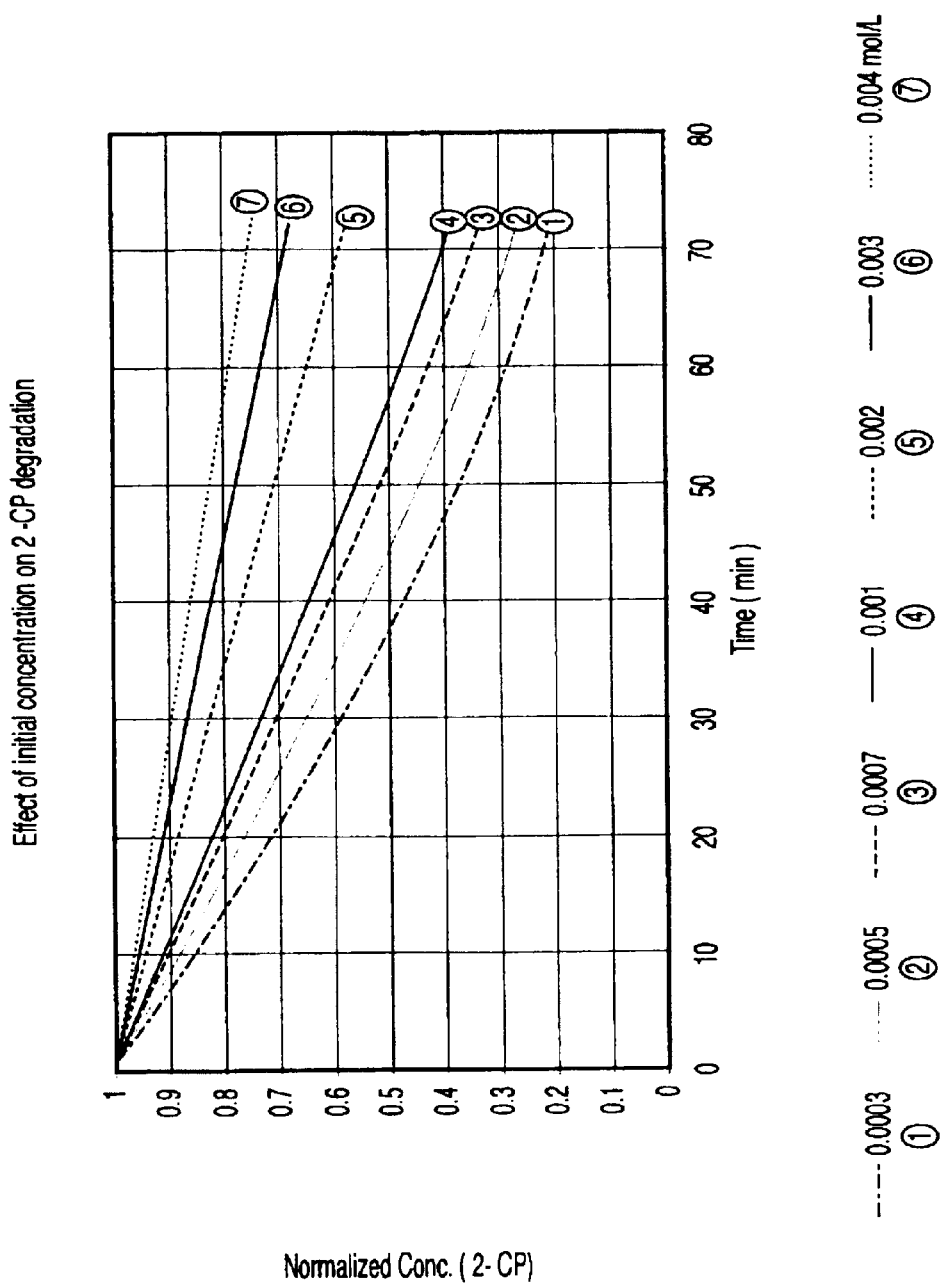
FIG. 3 illustrates the effect of initial concentration on 2-CP degradation.
Figure 4:
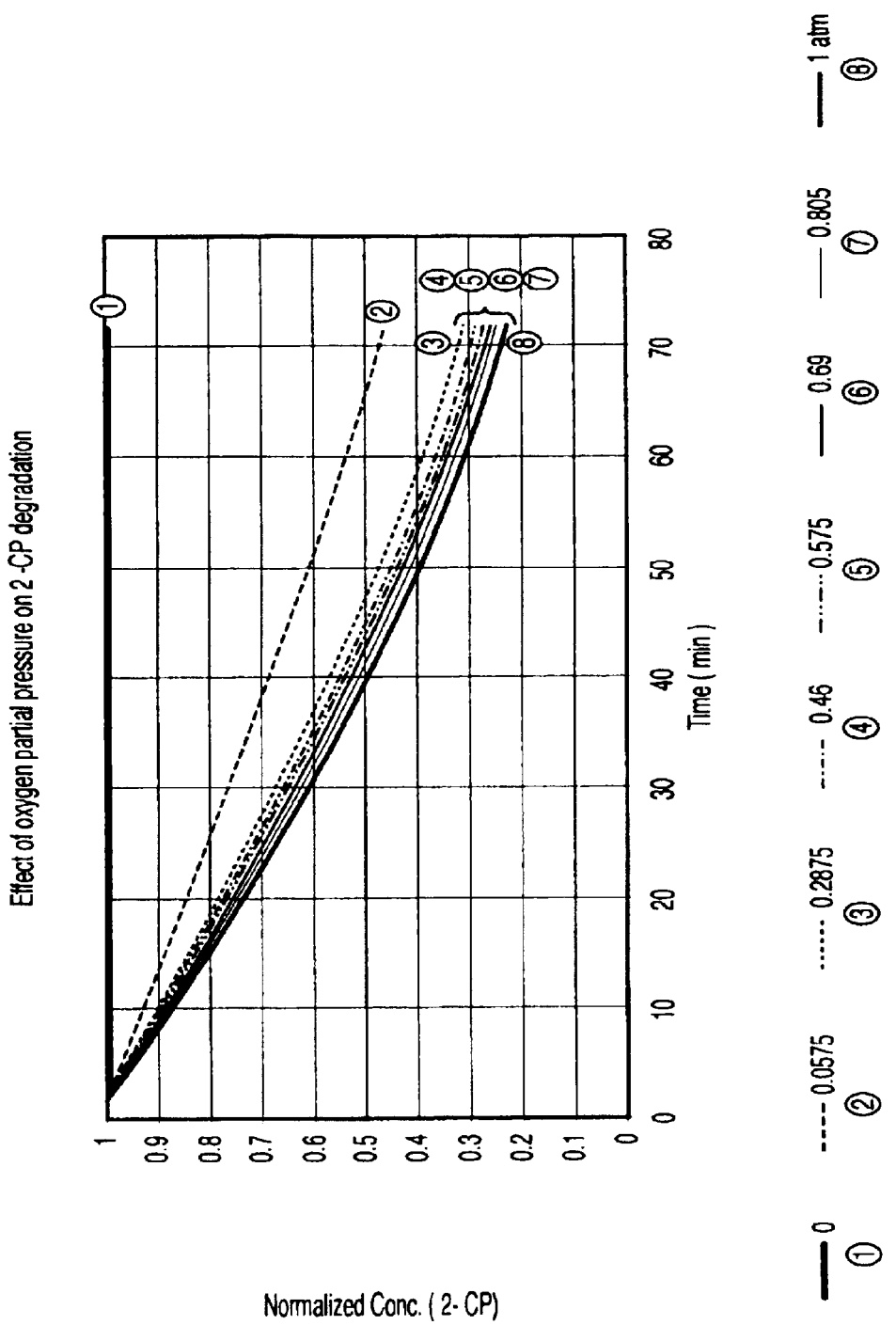
FIG. 4 illustrates the effect of oxygen partial pressure on 2-CP degradation.

The effect of initial concentration on 2-CP degradation was studied by maintaining the water recirculation rate at 27 lpm (when bed is fully expanded) and the initial 2-CP concentration was varied incrementally from 0.0003 to 0.004 mol/L. The effect of oxygen partial pressure on 2-CP degradation was studied by maintaining the water recirculation rate at 27 lpm and an initial 2-CP concentration of 0.0005 mol/L. The results of simulations for the once through process are presented in graphical form in FIGS. 3 and 4, respectively.

The trends observed with respect to the effect of initial concentration and oxygen partial pressure on 2-CP degradation satisfactorily match those obtained by Rideh et al. [7]. However, the values obtained do not match perfectly. While not wishing to be bound by any particular theory or mode of action, this is believed to be due to the following reasons: (a) the present reactor is much larger than that of Rideh et al., (b) Rideh et al. used the power emitted by the radiation source measured by uranyloxalate actinometry whereas a LSPP model was used in our study to arrive at the light intensity in a particular volume element under consideration, and (c) difference in the photocatalyst properties used in each study (e.g., particle size, particle density, etc.).

For studying the effect of operational parameters in dual mode process, the range of values of various operational parameters used in simulations are presented in Table 2.

Figure 5:
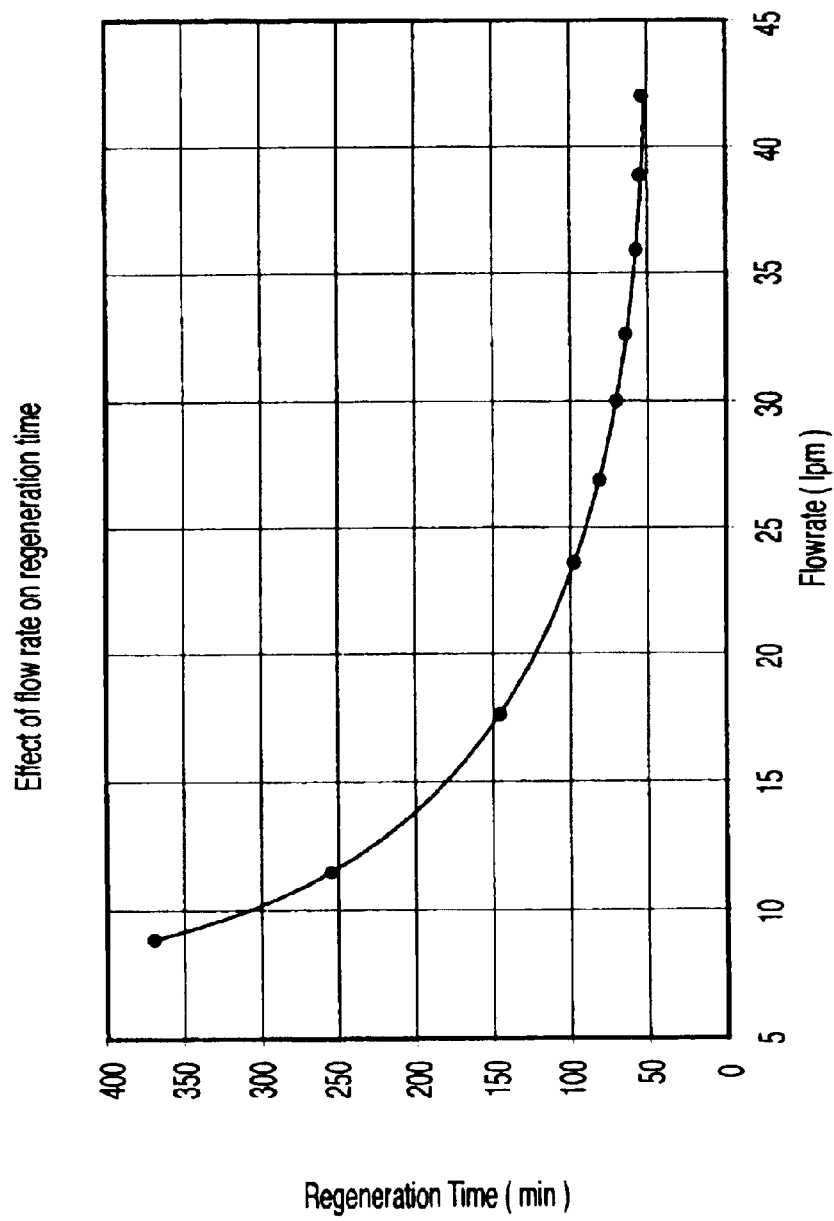
FIG. 5 illustrates the effect of flow rate on regeneration time.

The effect of varying water recirculation rate on regeneration time is depicted graphically in FIG. 5. As illustrated, there is a pronounced drop in regeneration time required when the flow rate is increased to a value where the bed is fully fluidized. This is believed to be due to the fact that, on increasing flow rates, the frequency of exposure of particles to irradiation increases. Also, the height offed exposed to irradiation increases and the decrease in particle density facilitates more effective capture of the incident radiation. The decrease in regeneration time is not so pronounced once the bed is fully expanded at a flow rate of 27 lpm, as the only beneficiary factor is the increase in frequency of exposure.

Figure 6:
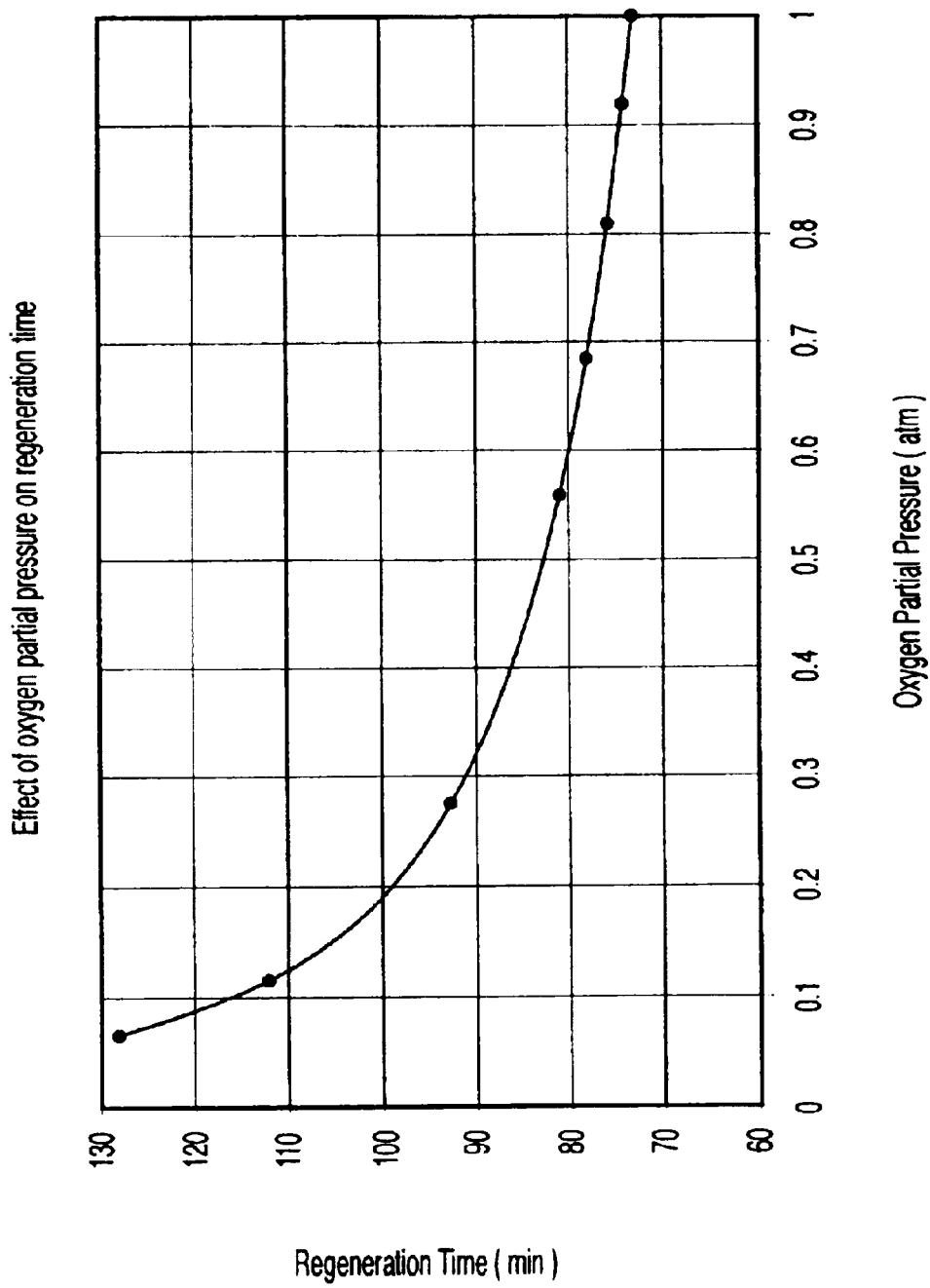
FIG. 6 illustrates the effect of oxygen partial pressure on regeneration time.

According to FIG. 6, there is a sharp nonlinear decrease in the regeneration time on increasing the oxygen partial pressure. It confirms the fact that the partial pressure of oxygen is a an important factor in the photocatalytic reaction and the limitation of the rate of photocatalytic degradation is conventionally attributed to the recombination of photogenerated electron-hole pairs. Since, oxygen adsorbed on titanium dioxide surface prevents the recombination process by trapping electrons, it can be inferred that the reaction rate is a function of the fraction of adsorption sites occupied by oxygen. Hence, oxygen adsorption becomes a governing factor at very low dissolved oxygen concentrations.

Figure 7:
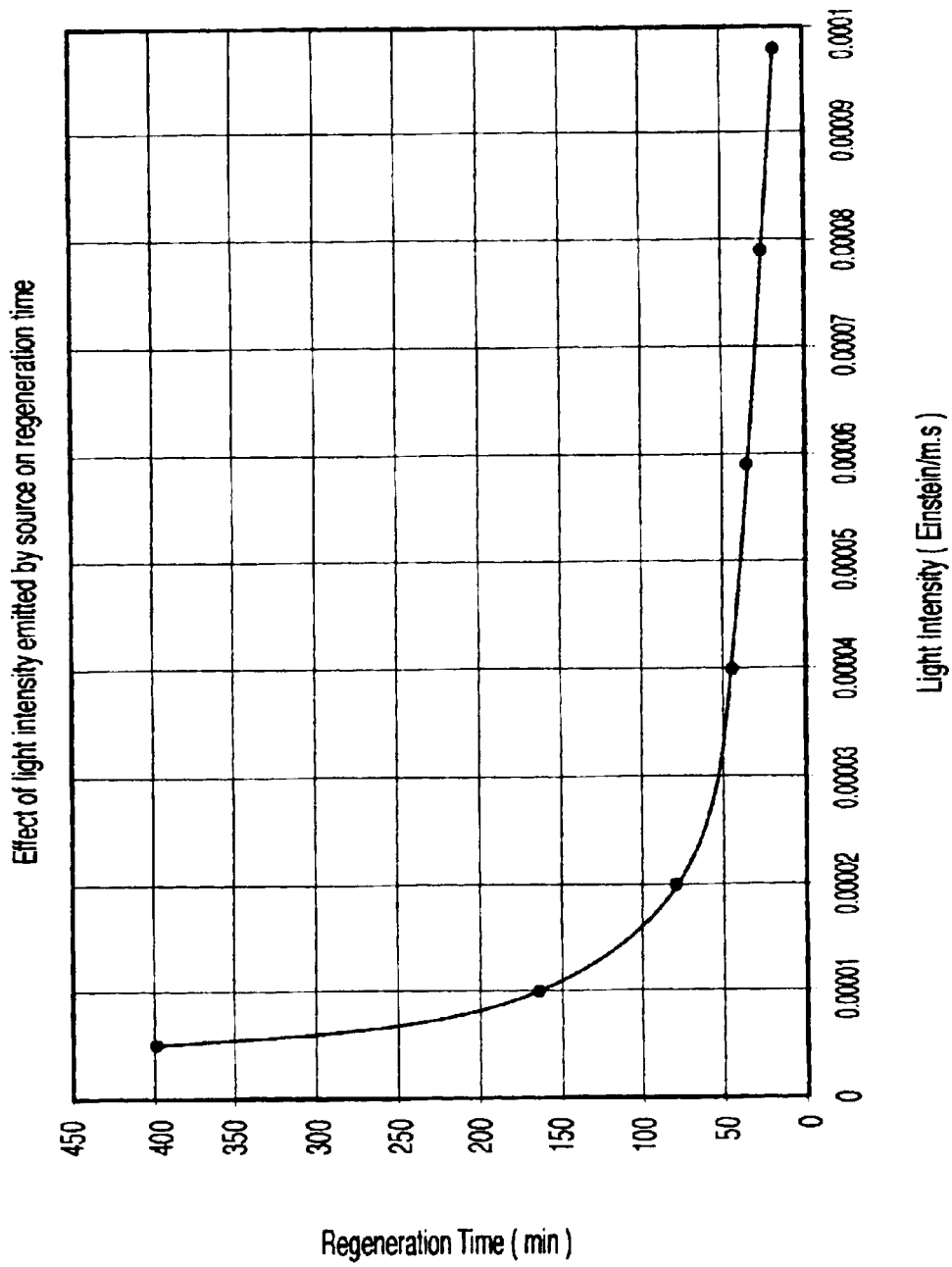
FIG. 7 illustrates the effect of light intensity emitted by source on regeneration time.

The results illustrated in FIG. 7 show an exponential decrease in the regeneration time required with an increase in the light intensity. The slope decreases after a certain value when it approaches saturation of the photocatalyst by the incident photons. Since, the annular irritated thickness is quite large in the reactor, the use of a very high intensity lamp is preferred to reach saturation. Of course, it is within the purview of those of skill in the art to reconcile lamp availability with power requirements with a view to optimizing reactor performance.

Figure 8:
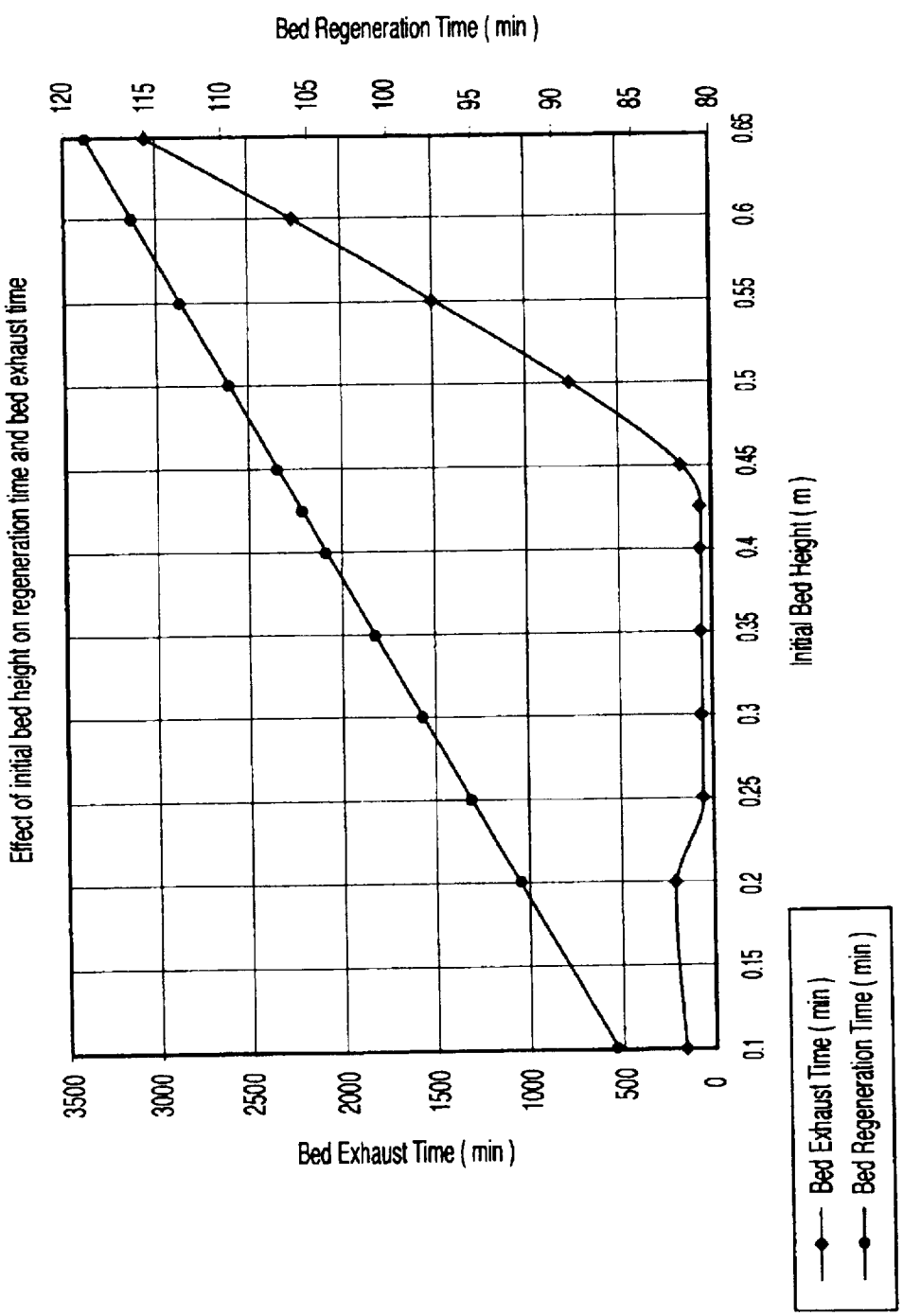
FIG. 8 illustrates the effect of initial bed height on regeneration time and bed exhaust time.

Simulations were carried out to study the effect of initial bed height on regeneration time and bed exhaust time, keeping the flow rates in both the modes constant at 27 lpm and a pollutant concentration of 0.0005 mol/L in the adsorption phase. The results shown in FIG. 8 depict that there is a substantially linear dependence of bed exhaust time with initial bed height and the slope will depend upon the flow rate and pollutant concentration in the adsorption cycle. The regeneration time is around 80 min. and remains about the same for initial bed heights of up to 0.4 m and then increases linearly for higher initial bed heights. The water recirculation rate of 27 lpm suffices to raise the initial bed height of 0.45 m to full expansion. The bed exhaust times are more than ten times-higher than regeneration times: so, there is a possibility of increasing the flow rates in adsorption by a factor of ten. This can serve to equalize the bed exhaust and bed regeneration times which will facilitate continuous operation of two units in parallel, one in adsorption and the other one in regeneration phase, switching over from one to another.

While the present invention has been described in detail including reference to the Examples, it will of course be readily understood that a number of modifications to the exemplified embodiment will be apparent to those of skill in the art with this specification in hand, which modifications do not depart from the spirit and scope of the present invention. For example, while reference to the preferred embodiments sets out a detailed description of a particular ultraviolet radiation device, a number of modifications and variations to the particular ultraviolet radiation device will be apparent to those of skill in the art, including the modifications and variations set out in the claims filed herewith.

All publications, patents and patent applications referred to herein are incorporated by reference in their entirety to the same extent as if each individual publication, patent application was specifically and individually indicated to be incorporated by reference in its entirety.

TABLE 1

| Parameter | Value |
| --- | --- |
| Mean particle diameter | 500.0 microns |
| Particle density | 3000.0 kg/m$^3$ |
| Sphericity of particles | 0.67 |
| Viscosity of water @ 25° C. | 0.001002 kg.m/s |
| Density of water @ 25° C. | 998.2 kg/m$^3$ |
| Molar absorption coefficient | 0.01 |
| Reactor length | 0.80 m |
| Inner radius of the reactor | 0.06 m |
| Outer radius of the reactor | 0.10 m |
| Initial bed height | 0.45 m |
| Voidage at min. fluidization | 0.49 |
| Oxygen partial pressure | 0.575 atm |
| Recirculation flow rate (regeneration cycle) | 27.0 lpm |
| Superficial velocity | 0.0224 m/s |
| Residence time | 0.595 min. |
| Power emitted by source | $1.98 \times 10^{-5}$ |
| α (Fraction of particles incident to light) | 0.50 |
| β (Fraction of incident light absorbed) | 0.75 |

TABLE 2

| Parameters | Values |
| --- | --- |
| Water recirculation rate | 9–42 L/min. |
| Oxygen partial pressure | 0.0575–1.0 atm |
| Power emitted by source | (3.96 × 10$^{-6}$)–(9.9 × 10$^{-5}$) Einstein/m.sec. |
| Initial bed height | 0.1–0.65 m |

CITED PRIOR ART REFERENCES

1. A. Haarstrick, O. M. Kut, E. Heinzel, Environ. Sci. Technol., 30 (1996), 817.
2. I. R. Bellobono, A. Carrara, B. Bami, A. Gazzotti, J. Photobiol. A: Chem., 84 (1994), 83.
3. a. P. Davis, in "Process Engineering for Pollution control and waste minimization", N.Y., 1994.
4. Y. Xu, Cooper H. Langford, J. Phys. Chem., 99 (1995), 11501.
5. W. Choi, A. Termin, M. R. Hoffman, J. Phys. Chem., 98 (1994), 13669.
6. A. Starosud, D. P. Bazett-Jones, Cooper H. Langford, Chem. Com. (1997), 443.
7. L. Rideh, A. Wehrer, D. Ronze, and A. Zoulalian, Ind. Eng. Chem. Res. 36 (1997), 4712.
8. C. Y. Wen, and Y. H. Yu, Fluid Particle Technology, Che. Eng. Prog. Symp. Ser., 52 (1966), 100.
9. P. R Harris, and J. S. Dranoff, AIChE J., 11 (1965), 497.
10. A. M Braun, L. Jakob, E. Oliveros, and C. A. O. Nascimento, Advances in Photochemistry, 18 (1993), 235.
11. S. M. Hassanien, H. Delmas, and J. P. Riba, Entropie, 119 (1984), 17.

NOMENCLATURE

2-CP 2-Chlorophenol
$\epsilon_{mf}$ voidage at minimum fluidization
$\mu_{\lambda,c}$ molar absorption coefficient
r radial distance, m
$\alpha$ fraction of particles irradiated by incident photons
A annular cross-sectional area, $m_2$
$\beta$ fraction of incident light intensity absorbed
$C_i$ pollutant concentration, mol/L
$C_L$ pollutant concentration in bulk liquid phase, mol/L
$C_S$ pollutant concentration on solid surface
$G_a$ Galileo number
$H_{EX}$ expanded bed height, m
$H_{mf}$ bed height at minimum fluidization, m
$I_{abs}$ absorbed light intensity, Einstein/L.s
$I_{inc}$ incident light intensity, Einstein/L.s
$k_L$ mass transfer coefficient
$K_{2\text{-}CP}$ adsorption constant for 2-CP
LSPP Line Source with Parallel Plane
Mv density number
$N_P$ total number of particles in the reactor
$n_p$ number of particles in elemental volume
$N_{PD}$ particle number density, particles/L
Q flow rate, L/s
$R_i$ inner radius of an annular photochemical reactor, m
$R_O$ outer radius of an annular photochemical reactor, m
$r_P$ mean particle radius, m
Sc Schmidt number
Sh Sherwood number
$S_{L,\lambda}$ photon rate of the light source per unit length, Einstein/m.s
$U_O$ supecrficial velocity of gas, m/s
$U_L$ superficial velocity of liquid, m/s

What is claimed is:

1. A process for reducing the level of a chemical compound in a fluid, the process comprising the steps of:
    feeding the fluid to a fluid treatment device comprising a fluid inlet; a fluid outlet and a flow-through fluid treatment zone disposed between the fluid inlet and the fluid outlet, the fluid treatment device comprising: a radiation source, an adsorbent and a photocatalyst;
    feeding the fluid in a first mode in which the fluid flows in a first direction and at least a portion of the chemical compound is adsorbed on the adsorbent; and
    feeding the fluid in a second mode in which the fluid flows in a second direction different from the first direction in which the adsorbed chemical compound is exposed to radiation from the radiation resulting in photooxidation of the chemical compound.

2. The process defined in claim 1, wherein, in the first mode, the adsorbent is utilized as fixed bed.

3. The process defined in claim 1, wherein, in the second mode, the photocatalyst comprises a fluidized bed.

4. The process defined in claim 1, wherein the photocatalyst comprises TiO.sub.2.

5. The process defined in claim 1, wherein the adsorbent comprises a zeolite.

6. The process defined in claim 1, wherein the adsorbent and the photocatalyst are comprised in the same particulate material.

7. The process defined in claim 1, wherein the radiation source comprises an ultraviolet radiation source.

8. The process defined in claim 1, wherein the fluid comprises water.

9. The process defined in claim 1, wherein the first direction and the second direction are substantially opposed to one another.

10. The process defined in claim 1, wherein the radiation source is operable only in the second mode.

11. The process defined in claim 1, wherein the chemical compound is organic.

12. The process defined in claim 1, wherein the chemical compound is inorganic.

13. The fluid treatment process defined in claim 1, comprising the additional step of switching from the first mode to the second mode when a predetermined amount of the chemical compound has been adsorbed on the absorbent.

14. The fluid treatment process defined in claim 1, comprising the additional step of switching from the second to the first mode when a predetermined amount of the chemical compound has been photocatalyzed.

* * * * *